United States Patent
Indradas et al.

(10) Patent No.: US 9,718,753 B2
(45) Date of Patent: Aug. 1, 2017

(54) PRO-FRAGRANCE COMPOUNDS

(71) Applicant: FIRMENICH SA, Geneva (CH)

(72) Inventors: Brinda Indradas, Plainsboro, NJ (US);
Gilbert Virtucio, Plainsboro, NJ (US);
Gary Womack, Plainsboro, NJ (US)

(73) Assignee: Firmenich SA, Geneva (CH)

(*) Notice: Subject to any disclaimer, the term of this patent is extended or adjusted under 35 U.S.C. 154(b) by 0 days.

(21) Appl. No.: 14/889,858

(22) PCT Filed: May 5, 2014

(86) PCT No.: PCT/EP2014/059130
§ 371 (c)(1),
(2) Date: Nov. 9, 2015

(87) PCT Pub. No.: WO2014/180791
PCT Pub. Date: Nov. 13, 2014

(65) Prior Publication Data
US 2016/0122271 A1    May 5, 2016

Related U.S. Application Data

(60) Provisional application No. 61/821,137, filed on May 8, 2013.

(51) Int. Cl.
| | | |
|---|---|---|
| *A61K 8/00* | (2006.01) |
| *C07C 43/166* | (2006.01) |
| *C07C 29/50* | (2006.01) |
| *C07C 45/36* | (2006.01) |
| *C11B 9/00* | (2006.01) |
| *C07C 43/215* | (2006.01) |
| *C11D 3/50* | (2006.01) |
| *C07C 43/23* | (2006.01) |
| *C07C 45/37* | (2006.01) |

(52) U.S. Cl.
CPC ............ *C07C 43/166* (2013.01); *C07C 29/50* (2013.01); *C07C 43/215* (2013.01); *C07C 43/23* (2013.01); *C07C 45/36* (2013.01); *C07C 45/37* (2013.01); *C11B 9/0003* (2013.01); *C11B 9/0015* (2013.01); *C11B 9/0019* (2013.01); *C11B 9/0061* (2013.01); *C11D 3/507* (2013.01); *C07C 2101/08* (2013.01); *C07C 2101/16* (2013.01)

(58) Field of Classification Search
CPC ............................ C07C 43/166; C07C 43/215
See application file for complete search history.

(56) References Cited

U.S. PATENT DOCUMENTS

2013/0316938 A1* 11/2013 Baumgartner .......... C07C 15/44
510/103

OTHER PUBLICATIONS

International Search Report and Written Opinion, application PCT/EP2014/059130, mailed Jul. 31, 2014.
Ambrogio et al., Organometallics 2008, 27, 3187-3195.
Bert, Comptes rendus Hebd. Séances Académie Sc., vol. 215, 1942, 187-188 (section of interest : last 2 lines p. 187 / first 2 lines p. 188).
Kasashima et al., Journal of Oleo Science., 2010, vol. 59, n° 10, 549-555.
Kim et al., J. Am. Chem. Soc. 1993, 115, 7653-7664.
Libor et al., Chemicky Prumysl, 1980, 30(3), 127-31.
Max et al., Recherches, 1937, 1, 13-15.

* cited by examiner

*Primary Examiner* — John Hardee
(74) *Attorney, Agent, or Firm* — Winston & Strawn LLP

(57) ABSTRACT

A compound is provided of Formula (I), wherein $R^1$ represents a $C_3$ to $C_{20}$ hydrocarbon group derived from an alcohol of formula $R^1OH$, from a formate of formula $R^1OCH=O$, or a cinnamyl aldehyde of Formula (II) wherein a compound of Formula I is capable of releasing a compound, when oxidized, selected from the group consisting of a fragrant alcohol of formula $R^1OH$, a fragrant formate ester of formula $R^1OCH=0$ and aryl aldehyde of Formula (III), wherein $R^2$ is, independently, hydrogen atom, hydroxyl group, optionally substituted $C_1$-$C_6$ alkyl group, $C_1$-$C_6$ alkoxy group, or $-0(C=0)CH(CH3)_2$ wherein any two of $R^2$ may form an optionally substituted 5 or 6 membered ring. The compounds are useful for example as a precursor for the prolonged delivery or release of fragrant compounds such as fragrant alcohols, fragrant aldehydes or fragrant formates.

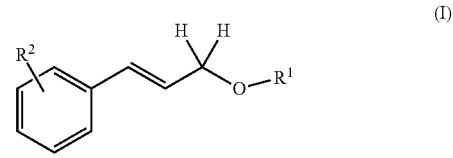

(I)

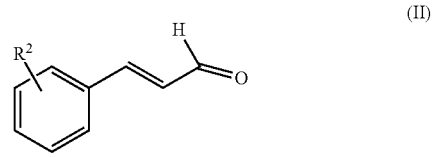

(II)

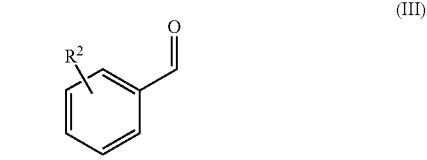

(III)

12 Claims, No Drawings

PRO-FRAGRANCE COMPOUNDS

FIELD

The present invention relates to the field of perfumery. More particularly, it concerns the use of cinnamyl ether compounds as precursors for the release of fragrant alcohols and aldehydes over a prolonged period.

BACKGROUND

The perfumery industry has a particular interest in compounds which are capable of being released over a prolonged time and that can deliver an odoriferous effect. Various means to control the release of fragrant compounds from pro-fragrances or precursor compounds have been reported. For example compounds have been reported that deliver a fragrance after they are hydrolyzed or exposed to light. In many applications it is desirable to begin and control the release of a fragrance at a time when an article or material containing the precursor is exposed to for example ambient oxygen. Hence, oxidizable pro-fragrances are desirable that can deliver a fragrance over a prolonged period of time after exposure to air.

SUMMARY

Provided herein is a compound of Formula (I)

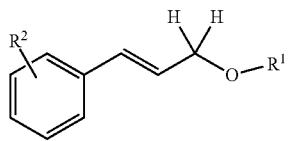
(I)

wherein $R^1$ represents a $C_3$ to $C_{20}$ hydrocarbon group derived from an alcohol of formula $R^1OH$, from a formate ester of formula $R^1OCH=O$, or from a cinnamyl aldehyde of Formula (II)

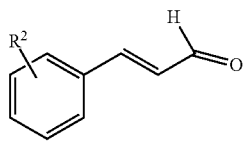
(II)

wherein a compound of Formula I is capable of releasing a compound, when oxidized, selected from the group consisting of a fragrant alcohol of formula $R^1OH$, a fragrant formate of formula $R^1OCH=O$ and a fragrant aryl aldehyde of Formula (III)

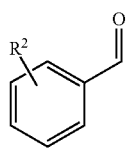
(III)

wherein $R^2$, is, independently, hydrogen atom, hydroxyl group, optionally substituted $C_1$-$C_6$ alkyl group, $C_1$-$C_6$ alkoxy group, or $-O(C=O)CH(CH3)_2$ wherein any two of $R^2$ may form an optionally substituted 5 or 6 membered ring.

Also provided herein is a method of releasing a fragrant compound from a precursor compound wherein the fragrant compound is selected from the group consisting of $R^1OH$, an aryl aldehyde of Formula (III) and a formate ester of formula $R^1OCH=O$:

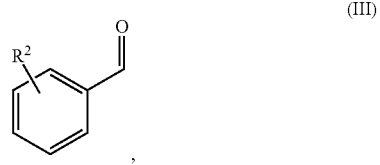
(III)

by exposing a precursor compound of Formula (I):

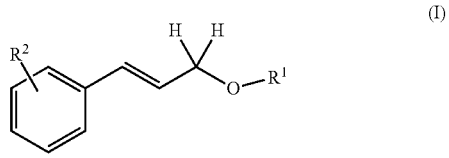
(I)

to an environment wherein the compound is oxidized and wherein:
$R^2$ is, independently, hydrogen atom, hydroxyl group, $-O(C=O)CH(CH3)_2$, optionally substituted $C_1$-$C_6$ alkyl group or $C_1$-$C_6$ alkoxy group, wherein any two of $R^2$ may form an optionally substituted 5 or 6 membered ring; $R^1$ represents a $C_1$ to $C_{20}$ hydrocarbon group derived from a fragrant alcohol of formula formula $R^1OH$, a fragrant formate of formula $R^1OCH=O$ and an aryl aldehyde of Formula (III).

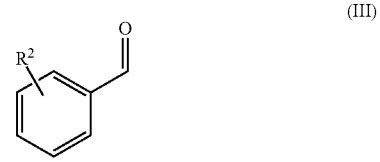
(III)

DETAILED DESCRIPTION

For the Summary, Description and Claims, the use of "or" means "and/or" unless stated otherwise. It is to be further understood that where descriptions of various embodiments use the term "comprising," those skilled in the art would understand that in some specific instances, an embodiment can be alternatively described using language "consisting essentially of" or "consisting of."

Further provided herein is a method wherein the method comprises the release of at least two compounds from the precursor compound, wherein at least one of the compounds is a fragrant compound wherein the two compounds are the same or different and each independently comprises the formula (III):

(III)

by exposing a precursor compound of Formula I:

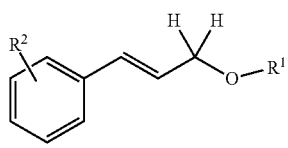

(I)

to an environment wherein the compound is oxidized and wherein:

$R^1$ represents a $C_3$ to $C_{20}$ hydrocarbon group derived from a cinnamyl alcohol or a cinnamyl aldehyde of Formula (IV)

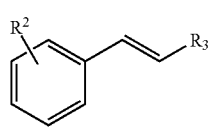

(IV)

wherein $R^2$ is, independently, hydrogen atom, hydroxyl group, optionally substituted $C_1$-$C_6$ alkyl group or $C_1$-$C_6$ alkoxy group, —O(C=O)CH(CH3)$_2$ wherein any two of $R^2$ may form an optionally substituted 5 or 6 membered ring; and $R^3$ is —CH$_2$OH or —CH=O.

It is understood that by "... hydrocarbon group..." it is meant that said group is consisting of hydrogen and carbon atoms and can be in the form of a linear, branched or cyclic, aromatic, alkyl, alkenyl, or alkynyl group, e.g., a linear alkyl group, or can also be in the form of a mixture of said type of groups, e.g. a specific group may comprise a linear alkyl, a branched alkenyl (e.g. having one or more carbon-carbon double bonds), a (poly)cyclic alkyl and an aryl moiety, unless a specific limitation to only one type is mentioned. Similarly, in all the embodiments of the invention, when a group is mentioned as being in the form of more than one type of topology (e.g. linear, cyclic or branched) and/or being saturated or unsaturated (e.g. alkyl, aromatic or alkenyl), it is meant also a group which may comprise moieties having any one of said topologies or being saturated or unsaturated, as explained above. Similarly, in all the embodiments of the invention, when a group is mentioned as being in the form of one type of saturation or unsaturation, (e.g. alkyl), it is meant that said group can be in any type of topology (e.g. linear, cyclic or branched) or having several moieties with various topologies.

It is understood that by "... alkyl group..." it is meant that said group is in the form of a linear, branched or cyclic alkyl group.

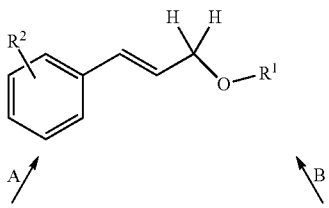

It is understood that a fragrant compound may originate from either side of a compound of Formula I and that the cinnamyl moiety (A) or the radical defined by $R^1$ (B) may generate a fragrant compound and that B may also be a cinnamyl moiety that is the same or different from (A). It is understood that both and (A) and (B) may both represent a cinnamyl moiety that will deliver two aryl aldehydes, either the same or different, with at least one of the aryl aldehydes being a fragrant compound. That is, the cinnamyl moiety (A) may or may not release a fragrant aryl aldehyde and the radical defined by $R^1$ also may represent a cinnamyl moiety which may or may not deliver a fragrant aryl aldehyde. When both A and B represent a cinnamyl moiety, whether the same or different, the distinction between A and B is interchangeable of course as governed by the geometry or configuration of the molecule. It is also understood that when B is not a cinnamyl moiety, it will be released as a fragrant compound.

In a particular embodiment a $C_1$-$C_6$ alkoxy group of a compound provided herein is selected from the group consisting of methoxy, ethoxy, propoxy, isopropoxy and butoxy group; more particularly the $C_1$-$C_6$ alkoxy group is methoxy group.

In another embodiment a $C_1$-$C_6$ alkyl group of a compound provided herein is selected from the group consisting of methyl, ethyl, propyl, isopropyl, butyl, isobutyl, tert-butyl, cyclopropyl, cyclopentyl and cyclohexyl group.

Optionally substituted means substituents, in relation to the $C_1$-$C_6$ alkyl group and 5 or 6 membered ring formed from the $C_1$-$C_6$ alkyl group, selected from the group consisting of methyl or dimethyl.

In a particular embodiment, a compound of Formula (I) is a para substituted cinnamyl ether derived from a tertiary alcohol radical.

The expression "derived from" is meant to include for example to be chemically derived (e.g., to produce or obtain a compound from another substance by a chemical reaction). It is also meant to include "represented by." It is also meant to include radicals for example that may be deduced or reasoned from the known literature that describes for example known compounds.

In one embodiment, a compound of Formula I is selected from the group consisting of (E)-(3-(2,6-dimethyloct-7-en-2-yloxy)prop-1-enyl)benzene; (E)-(3-(2,6-dimethyloct-7-en-2-yloxy)prop-1-enyl)benzene; (E)-(3-((3,7-dimethyloct-6-en-1-yl)oxy)prop-1-en-1-yl)benzene; (E)-(3-(cinnamyloxy)butyl)benzene; 1-(3-(2,6-dimethyloct-7-en-2-yloxy)prop-1-enyl)-4-methoxybenzene; 1-(3-(2,6-dimethyloctan-2-yloxy)prop-1-enyl)-4-methoxybenzene; 1-(3-(3,7-dimethylocta-1,6-dien-3-yloxy)prop-1-enyl)-4-methoxybenzene; 1-(3-(3,7-dimethyloct-1-en-3-yloxy)prop-1-enyl)-4-methoxybenzene; 1-methoxy-4-((E)-3-((1RS,2SR)-2-pentylcyclopentyloxy)prop-1-enyl)benzene; 1-(3-((2,6-dimethyloct-7-en-2-yl)oxy)prop-1-en-1-yl)-4-ethylbenzene; 4-(3-((2,6-dimethyloct-7-en-2-yl)oxy)prop-1-en-1-yl)-1,2-dimethoxybenzene; (E)-1-methoxy-4-(3-(4-phenylbutan-2-yloxy)prop-1-enyl)benzene; 1-methoxy-4-((E)-3-((E)-4-(2,6,6-trimethylcyclohex-2-enyl)but-3-en-2-yloxy)prop-1-enyl)benzene; and 1-(3-(3,7-dimethyloct-1-en-3-yloxy)prop-1-enyl)-4-methoxybenzene.

The precursor (pro-fragrance) compounds provided herein are in particular used as a precursor to deliver at least one fragrant compound. A fragrant compound provided herein means a compound which is capable of imparting an odor, in particular one which imparts an odor to a material, more particularly to a fabric or textile. The fragrant alcohols ($R^1$OH) released from a compound of Formula I or which Formula I is derived from ($R^1$OH) are meant to encompass any fragrant alcohol having more than three carbon atoms. While not providing an exhaustive list, provided here is a list of alcohols which are capable of imparting pleasant odors, particularly from surfaces, materials or even air. The fragrant alcohols may be selected from the group consisting such as, but not limited to: anisic alcohol, cinnamic alcohol, fenchylic alcohol, 9-decen-1-ol, phenethylol, citronellol 3-methyl-5-phenyl-1-pentanol (origin: Firmenich SA. Geneva. Switzerland), Mayol® ((4-isopropylcyclohexyl) methanol; origin: Firmenich SA. Geneva. Switzerland), 4-phenylbutan-2-ol, dihydromyrcenol (2,6-dimethyl-7-octen-2-ol), geraniol (3,7-dimethyl-2,6-octadien-1-ol), (Z)-3-hexen-1-ol, 1-hexanol, 2-hexanol, 5-ethyl-2-nonanol, 2,6-nonadien-1-ol, borneol, 1-octen-3-ol, 4-cyclohexyl-2-methyl-2-butanol (origin: Firmenich SA. Geneva. Switzerland), 2-methyl-4-phenyl-2-butanol, 2-methyl-1-phenyl-2-propanol, cyclomethylcitronellol, decanol, dihydroeugenol, 8-p-menthanol, 3,7-dimethyl-1-octanol, 2,6-dimethyl-2-heptanol, dodecanol, eugenol, Florol® (tetrahydro-2-isobutyl-4-methyl-4(2H)-pyranol; origin: Firmenich SA. Geneva. Switzerland), isoeugenol, linalool, Tarragol® (2-methoxy-4-propyl-1-cylohexanol; origin: Firmenich SA. Geneva, Switzerland), α-terpineol, tetrahydromuguol, 3,7-dimethyl-3-octanol, Lyral® (4-(4-hydroxy-4-methylpentyl)-cyclohex-3-ene-1-carbaldehyde: origin International Flavors and Fragrances. USA), Furaneol® (origin: Firmenich SA. Geneva. Switzerland), 5,6-dimethyl-1-methylethenylbicyclo[2.2.1]hept-5-ene-2-methanol (Arbozol), 2-phenyethanol, 1-phenylpropanol, 2-phenylpropanol, Lilyflore® ((2,5-dimethyl-2,3-dihydro-1H-inden-2-yl) methanol; origin: Firmenich SA. Geneva. Switzerland), 2,2-dimethyl-3-(3-methylphenyl)-propan-1-ol (Majantol), 2-pentylcyclopentanol, 7-hydroxy-3,7-dimethyloctanal (hydroxycitronellol), 1,1-dimethyl-2-phenylethanol, 4-cyclohexyl-2-methylbutan-2-ol, menthol, 2,6-dimethylheptan-2-ol, 2-tert-butylcyclohexanol, 4-tert-butylcyclohexanol, 2,6-dimethyl-3,5-octadien-2-ol (muguol), 2-methyl-6-methylene-7-octen-2-ol (myrcenol), 3,7,9-trimethyl-1,6-decadien-3-ol (isobutyl linalool), methyl salicylate, cis-3-hexenyl salicylate, 3,6-dimethyloctan-3-ol, 1,2-dimethyl-3-prop-1-en-2-ylcyclopentan-1-ol (plinol), 2-methyl-4-phenylpentanol (Pamplefleur), 3-methyl-5-phenylpentanol, 3-methyl-5-(2,2,3-trimethyl-1-cyclopent-3-enyl)pentan-2-ol (Sandalore®), (E)-3,3-dimethyl-5-(2,2,3-trimethyl-3-cyclopenten-1-yl)-4-penten-2-ol (Polysantol®), 1-(2,2,6-trimethylcyclohexyl)hexan-3-ol (Norlimbanol™), (E)-4-methyl-dec-3-en-5-ol, and 4-(4-hydroxyphenyl)butan-2-one.

A fragrant formate ester released from Formula I or which a formate ester ($R^1OCH{=}O$) of Formula I is derived from ($R^1OCH{=}O$) are meant to encompass any fragrant formate ester. In one aspect, the formate esters are selected from the group consisting of isopropyl formate, butyl formate, pentyl formate, isopentyl formate, 3-methylpentyl formate, hexyl formate, pipol formate, heptyl formate, octyl formate, octan-2-yl formate, nonan-2-yl formate, dodecyl formate, eugenol formate, isoeugenol formate, 4-methoxybenzyl formate, 1-phenylethyl formate, phenethyl formate, hydrocinnamyl formate, cinnamyl formate, β-naphthyl formate, menthyl formate, iso-pulegyl formate, nerolidyl formate, neryl formate, geranyl formate, linalyl formate, dihydromyrcenyl formate, myrcenyl formate, citronellyl formate, 2-methyl-1-phenylpropan-2-yl formate, ((3aR,4S,5R,7S,7aR)-octahydro-1H-4,7-methanoinden-5-yl)methyl formate, ((1R,5S)-6,6-dimethylbicyclo[3.1.1]hept-2-en-2-yl)methyl formate, 1-(3,3-dimethylcyclohexyl)ethyl formate, 3-mercapto-3-methylbutyl formate, (6,6-dimethyl-bicyclo[3.1.1]hept-2-en-2-yl)methyl formate, 2-phenylpropan-2-yl formate, vanillyl formate.

In another embodiment a non-limiting example of a fragrant aryl aldehyde released from a compound of Formula I is selected from the group consisting of: benzaldehyde, anisaldehyde, 4-methylbenzaldehyde, 4-ethylbenzaldehyde, 4-isopropylbenzaldehyde, 4-(tert-butyl) benzaldehyde, 2-methoxybenzaldehyde, 3,4-dimethoxybenzaldehyde, heliotropin, 4-hydroxybenzaldehyde, vanillin, 3-ethoxy-4-hydroxybenzaldehyde, 4-formyl-2-methylphenyl acetate, 4-formyl-2-methoxyphenyl isobutyrate, 3,5,5,6,7,8,8-heptanmethyl-5-6-7-8-tetrahydronaphthalene-2-carbaldehyde.

Many of these ingredients are in any case listed in reference texts such as the book by S. Arctander, Perfume and Flavor Chemicals, 1969, Montclair, N.J., USA, or its more recent versions, or in other works of a similar nature.

In another embodiment provided herein is a method to improve, enhance or modify odoriferous properties of a perfuming composition or a perfumed article, which method comprises adding to said composition or article an effective amount of a compound of Formula I.

In another embodiment, provided herein is a perfumed article comprising a compound provided herein wherein the perfumed article is provided in a perfumed product selected from the group consisting of perfume, cologne, bath gel, shower gel, hair-care product, cosmetic preparation, body deodorant, solid or liquid air-freshener, detergent, fabric softener, and all purpose cleaner.

In another embodiment provided herein is a method as described wherein a compound provided herein is exposed to the environment through a perfumed article comprising the compound wherein the perfumed article is provided in a perfumed product selected from the group consisting of perfume, cologne, bath gel, shower gel, hair-care product, cosmetic preparation, body deodorant, solid or liquid air-freshener, detergent, fabric softener, and all purpose cleaner.

In a particular embodiment the all purpose cleaner is an all purpose household cleaner, a window cleaner, a furniture polish, a fabric conditioner, softener or wash in form of a powder, a liquid or a tablet, a shampoo, a hair conditioner, a leave-in hair conditioner, or a hairspray.

A precursor compound of Formula I provided herein may be used for the controlled release of perfuming ingredients. This use, for example concerns a method to confer, enhance, improve or modify the odor properties of a perfuming composition, of an article or of a surface. In a particular embodiment, the pro-fragrance is applied to a material such as a fabric or textile upon the process of washing material or treating it with a fabric softener. In one aspect, the perfuming effect of such compounds can be to prolong and intensify a perfuming effect upon the exposure of the material to ambient air.

In another aspect, the controlled release of a perfuming alcohol or aldehyde provided herein comprises adding to a composition or an article an effective amount of a compound (I) which is capable of imparting an odor to fabrics or textiles when oxidized after the process of washing with a detergent or with the treatment of a fabric softener. The release of the fragrance provided herein is sustained particularly for a period of greater than 1 day, most particularly greater than 1 week, and even more particularly greater than 2 weeks. In many applications it is desirable to begin and control the release of a fragrance at a time when an article or material, containing the precursor or which the precursor has been deposited on, is exposed to for example ambient oxygen.

In another embodiment, provided herein is a fragrance delivery system comprising a compound of Formula I which provides a long-lasting odor of volatile fragrance from a product or from a product deposited on a material. The release of the above-mentioned fragrant compounds from the compounds and delivery system described herein occurs upon the exposure for example of a precursor compound according to Formula I to oxygen or other oxidizing agents.

In another embodiment, a compound or method provided herein can be used in functional perfumery. Particularly, the precursor compounds and methods provided herein can be used in applications such as liquid or solid detergents for the treatment of textiles and fabric softeners, in which the fragrance of the ingredients must be effectively imparted to the textile during washing.

In one aspect, the precursor compounds of Formula I provide, by release of the fragrant alcohol, fragrant formate ester or the fragrant aryl aldehyde, a noticeable fragrance to the laundry, produced by an odoriferous alcohol or aldehyde, which would not be detected on the laundry over a sufficiently long period if the alcohol or aldehyde had been used as it is, i.e. without a precursor.

The invention will now be described in further detail by way of the following examples. These examples are not intended to be limiting and are for illustrative purposes only.

EXAMPLES

Example 1

Cinnamyl Ethers by the Williamson Ether Synthesis

In a typical procedure, 27.9 mmol of alcohol was added to a stirring mixture of NaH (38.1 mmol, 60% in mineral oil) in THF (25 mlml), followed by cinnamyl bromide (25.4 mmol.). After an exotherm subsided, the mixture was stirred overnight at RT. After 24 h, water was added to quench any remaining NaH. The mixture was diluted in Et$_2$O, and after extracting with water, the organic phase was dried (MgSO$_4$), filtered and concentrated. Purification by silica gel flash chromatography (hexane/EtOAc) followed by bulb-to-bulb distillation yielded the cinnamyl ether as a colorless liquid.

Example 1.1 (E)-(3-(2,6-dimethyloct-7-en-2-yloxy)prop-1-enyl)benzene

Using 2,6-dimethyloct-7-en-2-ol (dihydromyrcenol), the product was obtained in 43% yield.

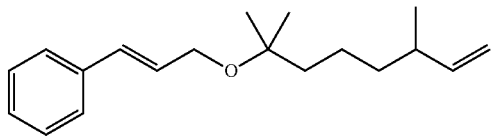 [SMILES: C=CC(C)CCCC(C)(C)OC/C=C/c1ccccc1]

$^1$H NMR (CDCl$_3$, 400 MHz): δ 0.98 ppm (d, 6.5 Hz, 3H), 1.19 (s, 6H), 1.24-1.40 (m, 4H), 1.45-1.55 (m, 2H), 2.06-2.19 (m, 1H), 4.03 (dd, J=1.60, 5.7 Hz, 2H), 4.90 (ddd, J=0.8, 1.8, 10.2, 1H), 4.95 (ddd, J=1.2, 1.8, 17.2, 1H), 5.69 (ddd, J=7.4, 10.2, 17.2 Hz, 1H), 6.27 (dt, J=5.7, 15.8 Hz, 1H), 6.58 (d, J=15.8 Hz, 1H), 7.14-7.39 (m, 5H).

MS (EI): 272, (M$^+$, <1), 228 (5) 135 (2), 134 (15), 117 (100), 115 (28), 105 (6), 83 (58), 69 (37), 57 (14), 55 (30), 41 (10).

Example 1.2 (E)-(3-(2,6-dimethyloct-7-en-2-yloxy)prop-1-enyl)benzene

Using 3,7-dimethyloct-1-en-3-ol (dihydrolinalool), the product was obtained in 30% yield.

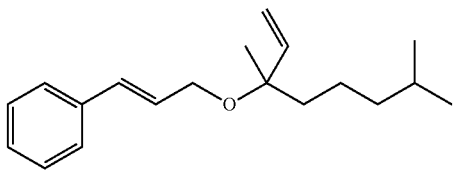 [SMILES: C=CC(C)(CCCC(C)C)OC/C=C/c1ccccc1]

$^1$H NMR (CDCl$_3$, 400 MHz): δ 0.87 (d, 6.6 Hz, 6H), 1.11-1.21 (m, 2H), 1.28 (s, 3H), 1.30-1.38 (m, 2H), 1.48-1.61 (m, 3H), 3.99 (dt, J=5.7, 1.5 Hz, 2H), 5.15 (dd, J=17.5, 1.3 Hz, 1H), 5.17 (dd, J=11.0, 1.3 Hz, 1H), 5.82 (dd, J=17.5, 11.0 Hz, 1H), 6.26 (dt, J=15.9, 5.7 Hz, 1H), 6.57 (d, J=15.9 Hz, 1H), 7.19-7.36 (m, 5H).

MS (EI): 272 (M$^+$, 1), 228 (9), 141 (4), 133 (3), 131 (3), 117 (100), 115 (24), 105 (8), 91 (11), 97 (9), 83 (37), 69 (24), 55 (17), 43 (9).

Example 1.3 (E)-(3-((3,7-dimethyloct-6-en-1-yl)oxy)prop-1-en-1-yl)benzene

Using citronellol, the product was obtained in 59% yield.

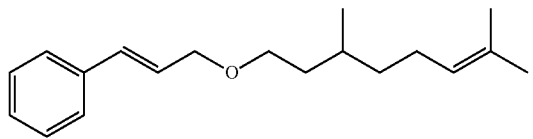 [SMILES: CC(C)=CCCC(C)CCOC/C=C/c1ccccc1]

$^1$H NMR (CDCl$_3$, 400 MHz): δ 0.90 (d, J=6.6 Hz, 3H), 1.11-1.22 (m, 1H), 1.30-1.47 (m, 2H), 1.53-1.73 (m, 2H), 1.59 (s, 3H), 1.67 (s, 3H), 1.89-2.07 (m, 2H), 3.45-3.54 (m, 2H), 4.11 (d, J=5.9 Hz, 2H), 5.10 (t, J=7.1 Hz, 1H), 6.8 (dt, J=15.9, 5.9 Hz, 1H), 6.59 (d, J=15.9 Hz, 1H), 7.18-7.37 (m, 5H).

MS (EI): 272 (M$^+$, <1), 155 (10), 137 (32), 117 (100), 115 (36), 105 (12), 95 (28), 81 (59), 69 (84), 55 (20), 41 (26).

Example 1.4 (E)-(3-(cinnamyloxy)butyl)benzene

Using 4-phenylbutan-2-ol, the product was obtained in 39% yield.

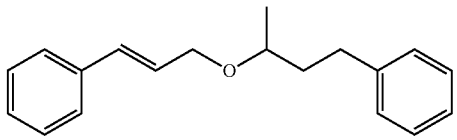 [SMILES: CC(CCc1ccccc1)OC/C=C/c1ccccc1]

$^1$H NMR (CDCl$_3$, 400 MHz): δ 1.21 (d, J=6.1 Hz, 3H), 1.69-1.96 (m, 2H), 2.61-2.82 (m, 2H), 3.51 (sextet, J=6.1 Hz, 1H), 4.07 (ddd, J=1.4, 6.0, 12.6 Hz, 1H), 4.20 (ddd, J=1.4, 6.0, 12.6 Hz, 1H), 6.30 (dt, J=6.0, 15.8 Hz, 1H), 6.59 (d, J=15.8 Hz, 1H), 7.11-7.42 (m, 10H).

MS (EI): 266 (M$^+$, 2), 162 (2), 134 (17), 133 (22), 117 (30), 115 (17), 105 (20), 103 (4), 92 (19), 91 (100), 77 (7), 65 (5).

Example 1.5 (S,E)-4-(3-((3,7-dimethyloct-6-en-1-yl)oxy)prop-1-en-1-yl)-2-methoxyphenol Using (E)-4-(3-hydroxyprop-1-enyl)-2-methoxyphenol (coniferyl alcohol) and (S)-(+)-citronellyl bromide, the product was obtained in 37% yield.

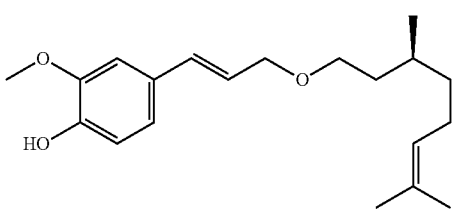 [SMILES: COc1cc(/C=C/COCC[C@@H](C)CCC=C(C)C)ccc1O]

¹H-NMR (CDCl₃, 400 MHz): δ 0.9 ppm (d, 6.3 Hz, 3H), 1.1-1.2 (m, 1H), 1.3-1.4 (m, 1H), 1.6 (s, 3H), 1.7 (s, 3H), 1.6-1.7 (m, 2H), 1.8-2.0 (m, 4H), 3.8 (s, 3H), 3.9-4.1 (m, 2H), 4.2 (d, J=5.8 Hz, 2H), 5.1 (t, 7.0 Hz, 1H), 6.2 (dt, 5.8, 15.9 Hz, 1H), 6.5 (d, 15.9 Hz, 1H), 6.7-6.9 (m, 3H).

MS (EI): 318 (60, M⁺), 180 (100), 164 (36), 152 (28), 137 (93), 124 (83), 91 (17), 83 (14), 69 (54), 55 (21).

Example 2

Cinnamyl Ethers by the Heck Reaction

Following a reported procedure (Ambrogio, I.; Fabrizi, G.; Cacchi, S.; Henriksen, S. T.; Fristrup, R.; Tanner, D.; Norrby, P.-O. *Organometallics* 2008, 27, 3187-3195), cinnamyl ethers were prepared by the Heck reaction between aryl halides and allyl ethers prepared from perfumery alcohols.

In a typical procedure, the perfume alcohol was slowly added to a mixture of NaH (60% in mineral oil) in DMF under a N₂ atm. Using an addition funnel, allyl bromide was added at a rate that allowed the ensuing exotherm to maintain the temperature of the mixture at about 70° C. The mixture was stirred an additional 15 min and then water was added. The mixture was diluted with diethyl ether, and after washing with water, the organic phase was dried with Na₂SO₄, filtered and concentrated. After silica gel flash chromatography, sometimes followed by bulb-to-bulb distillation, the allyl ethers were obtained as colorless liquids in yields of 29-90%.

The aryl halide was added to a mixture of the allyl ether, tetrabutylammonium acetate, palladium (II) acetate and DMF. The mixture was placed in a preheated 90° C. oil bath. The reaction progress was monitored by GC analysis and upon consumption of the aryl halide (0.5-2 h for aryl iodides and 16-24 h for aryl bromides), the reaction mixture was removed from the oil bath. Water and diethyl ether were added to the mixture and the resulting emulsion was filtered through a pad of Celite® prior to separating the phases. The ether phase was dried (Na₂SO₄), filtered and concentrated. Flash chromatography (silica gel) of the crude product (hexane/CH₂Cl₂/EtOAc) yielded colorless to pale amber oils that were composed predominantly of the para-methoxycinnamyl ethers. The other minor components were the corresponding enol ethers and the ether resulting from coupling at the internal alkene carbon. Spectral data are reported for just the (E)-para-methoxycinnamyl ethers.

Example 2.1 1-(3-(2,6-dimethyloct-7-en-2-yloxy)prop-1-enyl)-4-methoxybenzene

Starting from 2,6-dimethyloct-7-en-2-ol (dihydromyrcenol) (5 g, 32 mmol), allyl bromide (19.35 g, 160 mmol), DMF (27 mlml) and NaH (1.3 g, 32 mmol.), 2 g (10.2 mmol, 40% yield) of 7-(allyloxy)-3,7-dimethyloct-1-ene was obtained after flash chromatography. Using this allyl ether (5.6 g, 28.5 mmol), 1-iodo-4-methoxybenzene (5 g, 21.4 mmol), tetrabutylammonium acetate (10.7 g, 35.6 mmol), Pd(OAc)₂ (128 mg, 570 μmol) and DMF (25 mlml), 2.55 g (8.43 mmol, 39% yield) of an isomer mixture was obtained after flash chromatography (hexane/CH₂Cl₂/EtOAc: 100/0/0→50/50/0→09/0/1) containing 71% of the title compound (E/Z=12.8:1).

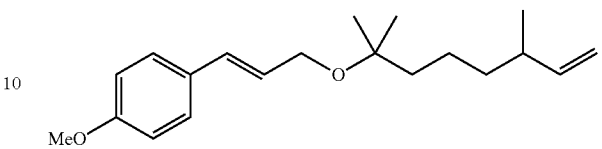

¹H NMR (CDCl₃, 400 MHz): δ 0.99 (d, J=6.9 Hz, 3H), 1.19 (s, 6H), 1.24-1.41 (m, 4H), 1.43-1.55 (m, 2H), 2.13 (m, 1H), 3.78 (s, 3H), 4.00 (dd, J=1.4, 6.0 Hz, 2H), 4.90 (ddd, J=0.8, 2.0, 10.3 Hz, 1H), 4.96 (ddd, J=1.2, 2.0, 17.3 Hz, 1H), 5.69 (ddd, J=7.6, 10.3, 17.3 Hz, 1H), 6.13 (dt, J=6.0, 15.9 Hz, 1H), 6.52 (d, J=15.9 Hz, 1H), 6.82 (d, J=8.8 Hz, 2H), 7.30 (d, J=8.8 Hz, 2H).

MS (EI): 302 (M⁺, 4), 220 (1), 164 (73), 163 (70), 147 (100), 135 (52), 121 (24), 115 (13), 108 (15), 103 (10), 91 (15), 83 (25), 69 (21), 55 (28).

Example 2.2 1-(3-(2,6-dimethyloctan-2-yloxy)prop-1-enyl)-4-methoxybenzene

Starting from 2,6-dimethyloctan-2-ol (tetrahydromyrcenol) (15 g, 95 mmol), allyl bromide (28.7 g, 237 mmol), DMF (70 mlml) and NaH (3.79 g, 95 mmol), 7.9 g (39.9 mmol, 42% yield) of 2-(allyloxy)-2,6-dimethyloctane was obtained after bulb-to-bulb distillation. The title compound was prepared using this allyl ether (7.9 g, 39.8 mmol), 1-iodo-4-methoxybenzene (7.5 g, 32.0 mmol), tetrabutylammonium acetate (16.1 g, 53.4 mmol), DMF (50 ml) and Pd(OAc)₂ (0.2 g, 0.9 mmol). After work up of the reaction mixture, the crude product was mixed with 1 M HCl for 24 h at rt to hydrolyze the minor enol ether isomers. This mixture was extracted with diethyl ether and the recovered product subjected to flash chromatography (hexane/EtOAc: 100/0→00/10) followed by bulb-to-bulb distillation (120-140° C., 100 mTorr) to afford 4.4 g (14.5 mmol, 45.2% yield) of a yellow oil composed of 85% of the title compound (E/Z=11.9:1).

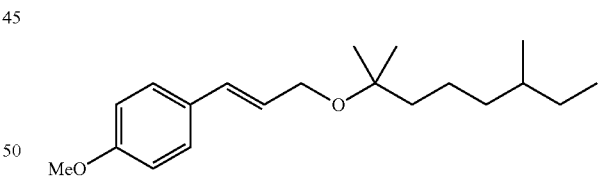

¹H NMR (CDCl₃, 400 MHz): δ 0.86 (d, J=6.4 Hz, 3H), 0.86 (t, J=7.2 Hz, 3H), 1.05-1.17 (m, 2H), 1.20 (s, 6H), 1.25-1.41 (m, 5H), 1.43-1.54 (m, 2H), 3.78 (s, 3H), 4.01 (dd, J=1.4, 6.0 Hz, 2H), 6.14 (dt, J=6.0 Hz, J=15.9 Hz, 1H), 6.52 (d, J=15.9, 1H), 6.82 (d, J=8.8 Hz, 2H), 7.30 (d, J=8.8 Hz, 2H).

MS (EI): 304 (M⁺, 4), 164 (74), 163 (59), 147 (100), 135 (44), 121 (23), 115 (13), 108 (16), 103 (10), 91 (15), 85 (17), 71 (17), 57 (21), 43 (18).

Example 2.3 1-(3-(3,7-dimethylocta-1,6-dien-3-yloxy)prop-1-enyl)-4-methoxybenzene Starting from 3,7-dimethylocta-1,6-dien-3-ol (linalool) (20.0 g, 130 mmol), allyl bromide (23.5 g, 194 mmol), DMF (25 ml), and NaH (7.78 g, 194 mmol), 12.7 g (65.4 mmol, 50.3% yield) of 3-(allyloxy)-3,7-dimethylocta-1,6-diene was obtained. Using this allyl ether (5.5 g, 28.5 mmol), 1-iodo-4-methoxybenzene (5 g, 21.4 mmol), tetrabutylammonium acetate (10.7 g, 35.6 mmol), Pd(OAc)$_2$ (0.1 g, 0.6 mmol), and DMF (60 ml), 2.3 g (7.7 mmol, 36% yield) of an isomer mixture was obtained after two consecutive flash chromatographies (hexane/EtOAc: 100/0→80/20→50/50; hexane/CH$_2$Cl$_2$: 100/0→98/2→70/30→0/100) comprising 98% of the title compound (E/Z=18.7:1).

and NaH (2.2 g, 53.8 mmol), 6.3 g (32.0 mmol, 56% yield) of (1RS,2SR)-1-(allyloxy)-2-pentylcyclopentane was obtained. Using this allyl ether (6.0 g, 32.0 mmol), 1-iodo-4-methoxybenzene (4 g, 17.1 mmol), tetrabutylammonium acetate (13.0 g, 43 mmol), DMF (40 ml) and Pd(OAc)$_2$ (0.15 g, 0.68 mmol), 1.9 g (6.3 mmol, 37% yield) of an isomer mixture was obtained after flash chromatography (Hexane/EtOAc: 100/0→85/15) comprising 88% of the title compound (E/Z=18:1).

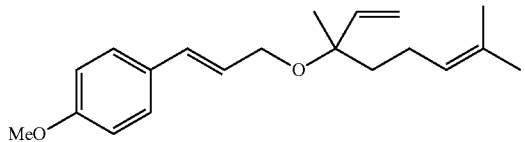 [SMILES: C=CC(C)(CCC=C(C)C)OC/C=C/c1ccc(OC)cc1]

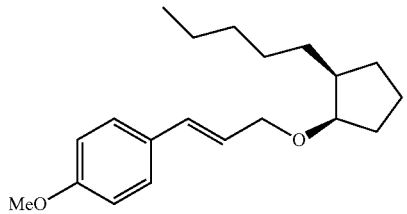

$^1$H NMR (CDCl$_3$, 400 MHz): δ 1.30 (s, 3H), 1.57-1.64 (m, 2H), 1.61 (s, 3H), 1.68 (s, 3H), 2.03 (q, J=8.0 Hz, 2H), 3.78 (s, 3H), 3.98 (d, J=5.8 Hz, 2H), 5.08-5.17 (m, 1H), 5.17 (dd, J=1.3, 17.3 Hz, 1H), 5.19 (dd, J=1.3, 11.2 Hz, 1H), 5.83 (dd, J=11.2, 17.3 Hz, 1H), 6.14 (dt, J=5.8, 15.8 Hz, 1H), 6.53 (d, J=15.8 Hz, 1H), 6.83 (d, J=8.8 Hz, 2H), 7.30 (d, J=8.8 Hz, 2H).

MS (EI): 300 (M$^+$, 1), 163 (100), 147 (81), 135 (55), 131 (13), 121 (15), 115 (13), 103 (10), 93 (13), 91 (22), 69 (27).

Example 2.4 1-(3-(3,7-dimethyloct-1-en-3-yloxy)prop-1-enyl)-4-methoxybenzene Starting from 3,7-dimethyloct-1-en-3-ol (dihydrolinalool) (8 g, 51.2 mmol), allyl bromide (12.4 g, 102 mmol), NaH (4.1 g, 102 mmol), and DMF (40 ml), 9 g (45.8 mmol, 90% yield) of 3-(allyloxy)-3,7-dimethyloct-1-ene was obtained. Using this allyl ether (11.0 g, 56.1 mmol), 1-iodo-4-methoxybenzene (7.5 g, 32.0 mmol), tetrabutylammonium acetate (24.16 g, 80 mmol), Pd(OAc)$_2$ (0.3 g, 1.3 mmol) and DMF (75 ml), 5.6 g (18.5 mmol, 58% yield) of an isomer mixture was obtained after two successive flash chromatographies (hexane/EtOAc: 100/0→20/80; hexane/EtOAc: 100/0→50/50) containing 84% of the title compound (E/Z=6.1:1).

$^1$H NMR (CDCl$_3$, 400 MHz): δ 0.88 (t, J=6.6 Hz, 3H), 1.15-1.95 (m, 15H), 3.79 (s, 3H), 3.79 (m, 1H), 3.99 (dd, J=6.0, 12.8 Hz, 1H), 4.15 (dd, J=6.0, 12.8 Hz, 1H), 6.14 (dt, J=6.0, 15.9 Hz, 1H), 6.53 (d, J=15.9 Hz, 1H), 6.84 (d, J=8.7 Hz, 2H), 7.31 (d, J=8.7 Hz, 2H).

MS (EI): 302 (M$^+$, 6), 164 (51), 148 (28), 147 (100), 135 (13), 121 (16), 115 (12), 108 (11), 97 (10), 91 (14), 83 (26).

Example 2.6 1-(3-((2,6-dimethyloct-7-en-2-yl)oxy)prop-1-en-1-yl)-4-ethylbenzene Starting from 2,6-dimethyloct-7-en-2-ol (dihydromyrcenol) (5.0 g, 32 mmol), allyl bromide (19.35 g, 160 mmol), DMF (27 ml) and NaH (1.3 g, 32 mmol.), 2 g (10.2 mmol, 40% yield) of 7-(allyloxy)-3,7-dimethyloct-1-ene was obtained after flash chromatography Using this allyl ether (7.5 g, 38.2 mmol), 1-ethyl-4-iodobenzene (4.4 g, 19.1 mmol), tetrabutylammonium acetate (14.4 g, 47.8 mmol), Pd(OAc)$_2$ (0.02 g, 0.08 mmol) and DMF (40 ml), 2.67 g (8.9 mmol, 23% yield) of an isomer mixture was obtained after flash chromatography (hexane/EtOAc: 100/0→96/4) containing 78.8% of the title compound (E/Z=11.6:1).

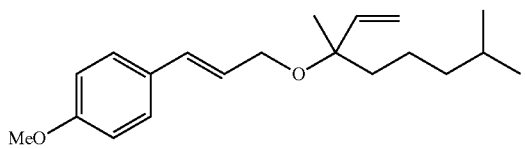 [SMILES: C=CC(C)(CCCC(C)C)OC/C=C/c1ccc(OC)cc1]

$^1$H NMR (CDCl$_3$, 400 MHz): δ 0.87 (d, J=6.6 Hz, 6H), 1.20-1.22 (m, 2H), 1.28 (s, 3H), 1.28-1.39 (m, 2H), 1.48-1.62 (m, 3H), 3.78 (s, 3H), 3.97 (d, J=5.8 Hz, 2H), 5.15 (dd, J=1.4, 17.5 Hz, 1H), 5.17 (dd, J=1.4, 11.0 Hz, 1H), 5.82 (dd, J=11.0, 17.5 Hz, 1H), 6.13 (dt, J=6.0, 15.9 Hz, 1H), 6.52 (d, J=15.9 Hz, 1H), 6.82 (d, J=8.8 Hz, 2H), 7.29 (d, J=8.8 Hz, 2H).

MS (EI): 302 (M$^+$, 3), 217 (5), 163 (70), 147 (100), 135 (85), 131 (10), 121 (10), 115 (13), 105 (8), 103 (10), 91 (17), 55 (18).

Example 2.5 1-methoxy-4-((E)-3-((1RS,2SR)-2-pentylcyclopentyloxy)prop-1-enyl)benzene Starting from (1RS,2SR)-2-pentylcyclopentanol (6 g, 38.4 mmol), allyl bromide (7.0 g, 57.6 mmol), DMF (60 ml)

$^1$H NMR (CDCl$_3$, 400 MHz): δ 0.99 (d, J=6.5 Hz, 3H), 1.20 (s, 6H), 1.21 (t, J=7.6 Hz, 3H), 1.24-1.41 (m, 4H), 1.43-1.53 (m, 2H), 2.06-2.18 (m, 1H), 2.61 (q, J=7.6 Hz, 2H), 4.01 (dd, J=1.5, 5.8 Hz, 2H), 4.90 (ddd, J=0.85, 2.0, 10.5 Hz 1H), 4.95 (ddd, J=1.24, 2.0, 17.0 Hz, 1H,), 5.69 (ddd, J=7.6, 10.5, 17.0 Hz, 1H), 6.22 (dt, 5.8, 15.9 Hz, 1H), (d, J=15.9 Hz, 1H), 7.11 (d, J=8.2 Hz, 2H), 7.28 (d, J=8.2 Hz, 2H).

MS (EI): 300 (M$^+$, 2), 256 (3), 218 (1), 162 (79), 145 (100), 133 (59), 117 (70), 115 (39), 83 (65), 69 (44), 55 (45).

Example 2.7 4-(3-((2,6-dimethyloct-7-en-2-yl)oxy)prop-1-en-1-yl)-1,2-dimethoxybenzene Starting from 2,6-dimethyloct-7-en-2-ol (dihydromyrcenol) (5 g, 32 mmol), allyl bromide (19.35 g, 160 mmol), DMF (27 ml) and NaH (1.3 g, 32 mmol), 2 g (10.2 mmol, 40% yield) of 7-(allyloxy)-3,7-dimethyloct-1-ene was obtained after flash chromatography. Using this allyl ether (4.5 g, 23.4 mmol), 4-bromo-1,2-dimethoxybenzene (2.5 g, 11.5 mmol), tetrabutylammonium acetate (8.3 g, 27.6 mmol), Pd(OAc)₂ (0.1 g, 0.46 mmol) and DMF (17 ml), 2.0 g (6.0 mmol, 52% yield) of an isomer mixture was obtained after flash chromatography (hexane/CH₂Cl₂/EtOAc: 100/0/0→97/3/0→95/0/5) containing 67% of the title compound (E/Z=10.2:1).

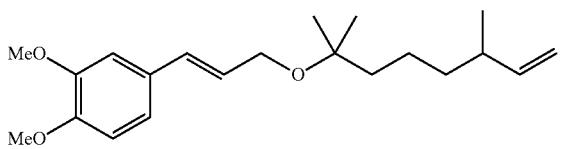 [SMILES: C=CC(C)CCCC(C)(C)OC/C=C/c1ccc(OC)c(OC)c1]

¹H NMR (CDCl₃, 400 MHz): δ 0.99 (d, J=6.6 Hz, 3H), 1.20 (s, 6H), 1.24-1.40 (m, 4H), 1.42-1.56 (m, 2H), 2.13 (m, 1H), 3.86 (s, 3H), 3.87 (s, 3H), 4.01 (dd, J=1.6, 6.0 Hz, 2H), 4.90 (ddd, J=0.8, 2.2, 10.3 Hz, 1H), 4.95 (ddd, J=1.2, 2.0, 17.4 Hz, 1H), 5.69 (ddd, J=7.4, 10.3, 17.2 Hz, 1H), 6.15 (dt, J=6.0, 15.7, 1H), 6.51 (d, J=15.7 Hz, 1H), 6.7 (d, J=8.3 Hz, 1H), 6.89 (dd, J=1.9, 8.3 Hz, 1H), 6.9 (d, J=1.9 Hz, 1H).

MS (EI): 332 (17), 194 (68), 193 (100), 177 (86), 165 (86), 151 (20), 146 (29), 138 (15), 131 (15), 83 (17), 69 (16), 55 (25).

Example 2.8 (E)-1-(3-((3,7-dimethyloctan-3-yl)oxy)prop-1-en-1-yl)-4-methoxybenzene Starting from 3,7-dimethyloctan-ol (tetrahydrolinalol) (8.8 g, 55.6 mmol), allyl bromide (13.4 g, 111 mmol), NaH (2.4 g, 61.2 mmol) and DMF (56 ml), 4.1 g (20.7 mmol, 33% yield) of 6-(allyloxy)-2,6-dimethyloctane was obtained. Using this allyl ether (4.1 g, 20.7 mmol), 1-iodo-4-methoxybenzene (2.3 g, 9.5 mmol), tetrabutylammonium acetate (7.18 g, 23.8 mmol), Pd(OAc)₂ (0.11 g, 0.5 mmol) and DMF (37 ml), 1.09 g (3.6 mmol, 38% yield) of the title compound was obtained after flash chomatography (hexane/EtOAc).

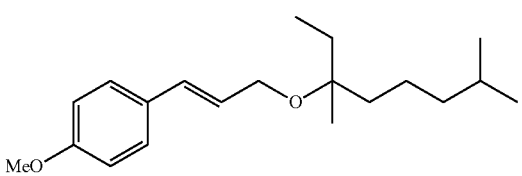 [SMILES: CCC(C)(CCCC(C)C)OC/C=C/c1ccc(OC)cc1]

¹H NMR (CDCl₃, 400 MHz): δ 0.87 (d, 6.7 Hz, 6H) 0.88 ppm (t, 7.3 Hz, 3H), 1.14 (s, 3H), 1.15-1.2 (m, 2H), 1.27-1.36 (m, 2H), 1.38-1.49 (m, 2H), 1.49-1.61 (m, 3H), 3.77 (s, 3H), 3.96 (d, J=5.9 Hz, 2H), 6.14 (dt, J=5.9 Hz, 15.9 Hz, 1H), 6.52 (d, J=15.9 Hz, 1H), 6.82 (d, J=8.8 Hz, 2H), 7.30 (d, J=8.8 Hz, 2H).

MS (EI): 304 (3, M⁺), 164 (51), 163 (25), 147 (100), 135 (20), 121 (19), 91 (13), 85 (15), 73 (12), 71 (15), 70 (13), 69 (15), 57 (15), 55 (16), 43 (17).

Example 3 para-Methoxycinnamyl Ethers by the Williamson Ether Synthesis

Example 3.1 (E)-1-methoxy-4-(3-(4-phenylbutan-2-yloxy)prop-1-enyl)benzene

Following a literature procedure Kim, T. Mirafzal, G. A.; Liu, J.; Bauld, N. L. *J. Am. Chem. Soc.*, 1993, 115 (17), pp 7653-7664, para-methoxycinnamyl bromide was prepared by adding a solution of PBr₃ (3.1 g, 11.4 mmol) in 10 ml CH₂Cl₂, dropwise to a solution of (E)-3-(4-methoxyphenyl)prop-2-en-1-ol (5.5 g, 33.5 mmol) in 20 ml CH₂Cl₂ cooled to −10° C. (ice/brine solution). After another 20 min of stirring at −10° C., 10 ml of cold saturated NaHCO₃ was added. The mixture was diluted with ether (200 ml) and washed with brine. The organic phase was dried (Na₂SO₄), filtered and concentrated to yield (E)-para-methoxycinnamyl bromide as pale yellow flakes. This was used immediately in the next step.

To a stirring mixture of NaH (1.25 g, 31.3 mmol) in DMF (25 ml) was added dropwise 4-phenylbutan-2-ol (3.35 g, 22.3 mmol). After stirring an additional 20 min, freshly prepared para-methoxycinnamyl bromide (7.61 g, 33.5 mmol) dissolved in DMF (10 ml) was added dropwise at a rate to maintain the temperature of the mixture at 40° C. (exothermic reaction). Excess NaH was quenched by the addition of water. After an additional 1 h of stirring at RT, the mixture was extracted with Et₂O with the aid of brine. The organic phase was dried (Na₂SO₄), filtered and concentrated. Two consecutive flash chromatographies (hexane/CH₂Cl₂/EtOAc: 100/0/0→70/30/0→50/50/0→98/0/2; hexane/CH₂Cl₂: 100/0→66/33→33/66) yielded 0.64 g (2.2 mmol, 10% yield) of the title compound as a colorless oil.

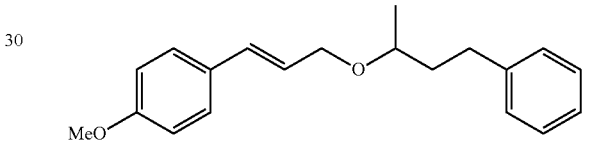

¹H NMR (CDCl₃, 400 MHz): δ 1.21 (d, J=6.2 Hz, 3H), 1.69-1.80 (m, 1H), 1.84-1.96 (m, 1H), 2.62-2.81 (m, 2H), 3.51 (sextet, J=6.2 Hz, 1H), 3.79 (s, 3H), 4.05 (dd, J=6.2, 12.3 Hz, 1H), 4.18 (dd, J=6.2, 12.3 Hz, 1H), 6.17 (dt, J=6.2, 15.9 Hz, 1H), 6.54 (d, J=15.9 Hz, 1H), 6.85 (d, J=8.8 Hz, 2H), 7.14-7.29 (m, 5H), 7.32 (d, J=8.8 Hz, 2H).

MS (EI): 296 (M⁺, 14), 163 (100), 147 (42), 135 (87), 121 (22), 117 (11), 115 (16), 108 (14), 105 (18), 103 (17), 91 (96).

Example 3.2 1-methoxy-4-((E)-3-((E)-4-(2,6,6-trimethylcyclohex-2-enyl)but-3-en-2-yloxy)prop-1-enyl)benzene Using the procedure described for Ex. 3.1, 2.4 g (6.9 mmol, 20% yield) of the title compound (dr=1:1) was prepared from (E)-para-methoxycinnamyl bromide (7.8 g, 34.3 mmol), (E)-4-(2,6,6-trimethylcyclohex-2-enyl)but-3-en-2-ol (α-ionol) (7.3 g, 37.8 mmol), DMF (40 ml) and NaH (1.9 g, 48.1 mmol).

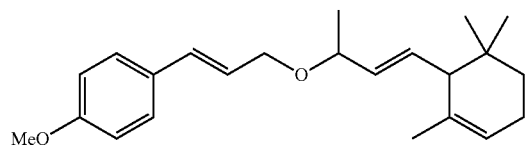 [SMILES: COc1ccc(/C=C/COC(C)/C=C/C2C(C)=CCCC2(C)C)cc1]

¹H NMR (CDCl₃, 400 MHz): δ 0.82, 0.88, 0.90 and 0.91 (all s, 6H), 1.12-1.23 (m, 1H), 1.277 and 1.281 (both d, J=6.4 Hz, 3H), 1.38-1.50 (m, 1H), 1.58 and 1.64 (both br s, 3H), 2.0 (m, 2H), 2.13 (m 1H), 3.78 (s, 3H), 3.88-4.00 (m, 2H), 4.13-4.20 (m, 1H), 5.32-5.47 (m, 3H), 6.09-6.21 (m, 1H), 6.50 and 6.52 (both d, J=15.9 Hz, 1H), 6.83 (d, J=8.8 Hz, 2H), 7.28-7.34 (m, 2H).

MS (EI): 340 (M$^+$, 6), 177 (10), 176 (9), 163 (50), 148 (100), 147 (88), 135 (40), 121 (36), 107 (16), 95 (22), 93 (23), 91 (29).

Example 3.3 1-(3-(3,7-dimethyloct-1-en-3-yloxy) prop-1-enyl)-4-methoxybenzene

Using the procedure described for Ex. 3.1, 2.1 g (6.9 mmol, 24.7% yield) of the title compound was prepared from NaH (1.1 g, 28 mmol), DMF (30 ml), para-methoxycinnamyl bromide (7.0 g, 30.8 mmol) and 3,7-dimethyloct-1-en-3-ol (dihydrolinalool) (8.8 g, 56.0 mmol). Spectral data were identical to those reported for Ex. 2.4.

Example 4

Application in Fabric Softener with Line Drying

A top-loading washing machine (Maytag, Model LS7806) was set to rinse and allowed to fill half full with water. 30 g an ester-quat type fabric softener base was prepared with the following composition: 12.2 wt % Stepantex® VL 90 (Stepan), 0.4 wt % (10% aqueous CaCl$_2$) and 87.4 wt % deionized water, containing 0.5 mmol of profragrance (or for controls, 0.5 mmol each of the expected alcohol and aryl aldehyde or alcohol/ketone and aryl aldehyde) was added. The drum was allowed to fill. Cotton terry towels (2.5 kg) were added and allowed to stand for 3 min prior to continuing agitation. Upon completion of the rinse and spin cycles, the towels were line-dried for 24 h at RT. The towels were stored in large plastic bins with lids (Sterilite 63 L) until olfactive panel evaluations were conducted 7 days after deposition.

Profragrance and control towels were presented to each panelist in number-coded bins and the panelists were asked to select the towels which had the stronger odor. In all cases, the majority of panelist chose the profragrance-treated towels as having the stronger odor (Table 1), demonstrating the controlled release effect of the precursors.

TABLE 1

Forced choice comparison between control towels and precursor-treated towels 7 days after deposition

| precursor | times profragrance was selected stronger/number of panelists | composition of control fabric softener |
|---|---|---|
| Ex. 2.1 | 12/15 | 0.5 mmol dihydromyrcenol, 0.5 mmol anisaldehyde |
| Ex. 2.2 | 12/16 | 0.5 mmol tetrahydromyrcenol, 0.5 mmol anisaldehyde |
| Ex. 2.4 | 14/15 | 0.5 mmol dihydrolinalool, 0.5 mmol anisaldehyde |
| Ex. 3.2 | 15/15 | 0.5 mmol α-ionol, 0.5 mmol α-ionone, 0.5 mmol anisaldehyde |

Example 5

Dynamic Headspace Analysis from Fabric Softener Application a) Deposition:

The ether profragrance (0.2 mmol) was added to 9 g of fabric softener base described in Ex. 4 and the mixture was rinsed into a 4 L beaker with water and if necessary with 1 ml of acetone. The beaker was then filled to 3 L total volume with water. Six, 5.0 g cloth squares (cotton fabric, weight 270 g/m$^2$, item 403 from Testfabrics, West Pittston, Pa.) were placed in the 4 L beaker and manually agitated for 3 min. After an additional 2 min of standing, the cloths were removed and the excess water squeezed out. The cloths were hung to dry for 24 h at RT and individually encased in aluminum foil until analyzed. This procedure was repeated for a duplicate set of samples. Control clothes were prepared by the same process using 0.2 mmol each of the expected volatiles (alcohol, formate ester and aryl aldehyde).

b) Analysis:

Dynamic headspace analyses of dried swatches were performed in duplicate at 1, 3 and 7 days after deposition. The swatch to be analyzed was placed inside a thermostatted (25° C.), headspace sampling cell to which a clean Tenax® cartridge was attached. A constant flow of air (200 ml/min) was drawn through the sampling cell and Tenax® cartridge using an air sampling pump. Prior to entering the sample cell, the air was drawn through a plug of active charcoal and then through a saturated NaCl solution to maintain a constant relative humidity of 75%. The swatches were sampled for 15 min at 0-15, 15-30 min using a clean Tenax® cartridge for each time period. For examples 3.1, 3.2 and 3.6, collection times were reduced to 0-7.5 min, 7.5-15 min, 15-22.5 min and 22.5-30 min to minimize overloading of the gc analytical column.

The cartridges were thermally desorbed (Perkin Elmer Turbo Matrix 650) and analyzed by GC-MS (Agilent 6890/5975C). The MSD (EI, 70 eV) was operated in the selected ion monitoring mode for quantitative measurements and in the full-scan mode for qualitative analysis. The GC was equipped with a Varian VF-1 ms capillary column (30 m, 0.25 mm i.d. 0.25 μm film). The desorber parameters were: valve temperature 240° C., desorption temperature 240° C., transfer line 250° C., trap −30° C. to 250° C. at 40° C./sec, purge time 1.0 min, desorption time 5 min, trap hold time 5 min, trap desorption flow time 0 min, cycle time 13 min, outlet split (5.2% injected), column flow 1.1 ml/min, desorption flow 50 ml/min. The GC oven temperature profile was: 60° C. (1 min hold) to 260° C. at 20° C./min (2 min hold). The volatile compounds formed by the decomposition of the precursor cinnamyl ethers are listed in Table 2.

c) Calculation:

The amount of each fragrance volatile collected is reported in Table 3 as the average headspace concentration (ng/L of air) over the 30 min collection period. The headspace concentrations were determined using linear external-standard calibration curves. At least four acetone solutions were prepared with concentrations ranging from 0.5 mM to 20 mM. The solutions were injected (0.2 μL) onto Tenax® cartridges and desorbed as described above. Each solution was analyzed in duplicate. Calibration curves were forced through the origin.

TABLE 2

Most abundant volatiles released by the tested cinnamyl ethers as determined by dynamic headspace analysis

| precursor | volatiles |
|---|---|
| Ex. 1.1[a] | dihydromyrcenol, dihydromyrcenyl formate, benzaldehyde, cinnamaldehyde |
| Ex. 2.1 | dihydromyrcenol, dihydromyrcenyl formate, anisaldehyde |
| Ex. 2.2 | tetrahydromyrcenol, tetrahydromyrcenyl formate, anisaldehyde |
| Ex. 2.3 | linalool, linalyl formate, anisaldehyde |

TABLE 2-continued

Most abundant volatiles released by the tested cinnamyl ethers as determined by dynamic headspace analysis

| precursor | volatiles |
|---|---|
| Ex. 2.4 | dihydrolinalool, dihydrolinalyl formate, anisaldehyde |
| Ex. 2.5 | 2-pentylcyclopentanol, 2-pentylcyclopentyl formate, anisaldehyde |
| Ex. 2.6 | dihydromyrcenol, dihydromyrcenyl formate, 4-ethylbenzaldehyde |
| Ex. 3.1 | 4-phenylbutan-2-ol, 4-phenylbutan-2-yl formate, anisaldehyde |

TABLE 3

Headspace concentrations (ng/L) of volatiles released from the precursor-treated towels or the corresponding control towels (controls in parentheses) at 1, 3 and 7 days after deposition

| precursor | perfume alcohol | | | formate ester | | | aryl aldehyde | | |
|---|---|---|---|---|---|---|---|---|---|
| | 1 d | 3 d | 7 d | 1 d | 3 d | 7 d | 1 d | 3 d | 7 d |
| Ex. 1.1[a] | 57 | 383 | 496 | 16 | 94 | 72 | 46 | 135 | 135 |
| | (0.5) | (0.5) | (0.5) | (4) | (2) | (1) | ( )[b] | (—) | (—) |
| Ex. 2.1 | 101 | 714 | 447 | 68 | 362 | 178 | 32 | 52 | 16 |
| | (0.5) | (0.5) | (0.5) | (4) | (2) | (1) | (2) | (3) | (7) |
| Ex. 2.2 | 133 | 816 | 469 | 53 | 626 | 356 | 62 | 98 | 6 |
| | (0.4) | (1) | (2) | (2) | (12) | (5) | (2) | (3) | (7) |
| Ex. 2.3 | 31 | 195 | 70 | 10 | 6.6 | 50 | 36 | 32 | 7 |
| | (0) | (2) | (2) | (0) | (0) | (0) | (2) | (3) | (7) |
| Ex. 2.4 | 40 | 253 | 132 | 17 | 41 | 47 | 32 | 33 | 11 |
| | (0.3) | (2) | (1) | (3) | (9) | (0) | (2) | (3) | (7) |
| Ex. 2.5 | 40 | 436 | 518 | 36 | 376 | 383 | 58 | 38 | 72 |
| | (21) | (21) | (50) | (36) | (14) | (17) | (12) | (12) | (13) |
| Ex. 2.6 | 111 | 632 | 398 | 19 | 83 | 41 | 111 | 371 | 304 |
| | (0.5) | (0.5) | (0.5) | (4) | (2) | (1) | (0.1) | (0.4) | (0.4) |
| Ex. 3.1 | 5 | 26 | 78 | 13 | 139 | 285 | 26 | 54 | 127 |
| | (1) | (4) | (3) | (0.1) | (0.2) | (0.3) | (2) | (3) | (7) |

[a]Cinnamaldehyde also was detected in the headspace, but was not quantitated.
[b]Benzaldehyde was not added to the control sample to allow for the analysis.

The invention claimed is:

1. A compound selected from the group consisting of (E)-(3-(2,6-dimethyloct-7-en-2-yloxy)prop-1-enyl)benzene; (E)-(3-(2,6-dimethyloct-7-en-2-yloxy)prop-1-enyl)benzene; (E)-(3-((3,7-dimethyloct-6-en-1-yl)oxy)prop-1-en-1-yl)benzene; (E)-(3-(cinnamyloxy)butyl)benzene; 1-(3-(2,6-dimethyloct-7-en-2-yloxy)prop-1-enyl)-4-methoxybenzene; 1-(3-(2,6-dimethyloctan-2-yloxy)prop-1-enyl)-4-methoxybenzene; 1-(3-(3,7-dimethylocta-1,6-dien-3-yloxy)prop-1-enyl)-4-methoxybenzene; 1-(3-(3,7-dimethyloct-1-en-3-yloxy)prop-1-enyl)-4-methoxybenzene; 1-methoxy-4-((E)-3-((1RS,2SR)-2-pentylcyclopentyloxy)prop-1-enyl)benzene; 1-(3-((2,6-dimethyloct-7-en-2-yl)oxy)prop-1-en-1-yl)-4-ethylbenzene; 4-(3-((2,6-dimethyloct-7-en-2-yl)oxy)prop-1-en-1-yl)-1,2-dimethoxybenzene; (E)-1-methoxy-4-(3-(4-phenylbutan-2-yloxy)prop-1-enyl)benzene; 1-methoxy-4-((E)-3-((E)-4-(2,6,6-trimethylcyclohex-2-enyl)but-3-en-2-yloxy)prop-1-enyl)benzene; and 1-(3-(3,7-dimethyloct-1-en-3-yloxy)prop-1-enyl)-4-methoxybenzene.

2. A product selected from the group consisting of perfume, cologne, bath gel, shower gel, hair-care product, cosmetic preparation, body deodorant, solid or liquid air freshener, detergent, fabric softener, and all-purpose cleaner which contains therein a precursor compound according to claim 1, wherein the precursor compound release a fragrant compound upon exposure to an environment which oxidizes the precursor compound to release the fragrant compound and provide a perfuming effect to the product.

3. The product of claim 2 wherein the fragrant compound is an alcohol, aryl aldehyde or formate ester which is derived from the precursor compound and which is released during use of the product.

4. A method of releasing a fragrant compound from a precursor compound by exposing a precursor compound according to claim 1 to an environment wherein the compound is oxidized to release an alcohol, aryl aldehyde or formate ester that prolongs or intensifies the perfuming effect of the precursor compound.

5. The method as recited in claim 4 wherein the compound is exposed to the environment through a perfumed article comprising the compound wherein the perfumed article is provided in a perfumed product selected from the group consisting of perfume, cologne, bath gel, shower gel, hair-care product, cosmetic preparation, body deodorant, solid or liquid air freshener, detergent, fabric softener, and all-purpose cleaner.

6. The method as recited in claim 5 wherein the all-purpose cleaner is an all-purpose household cleaner, a window cleaner, a furniture polish, a fabric conditioner, softener or wash in form of a powder, a liquid or a tablet, a shampoo, a hair conditioner, a leave-in hair conditioner, or a hairspray.

7. A method to improve, enhance or modify odoriferous properties of a perfuming composition or a perfumed article, which method comprises adding to said composition or article an effective amount of a precursor compound according to claim 1 to improve, enhance or modify the odor of the perfuming composition or perfumed article.

8. The method of claim 7, which further comprises providing the odor by release releasing a fragrant compound from the precursor compound upon exposure of the perfuming composition or perfumed article to an environment which oxidizes the precursor compound.

9. The method of claim 8 wherein the fragrant compound is an alcohol, aryl aldehyde or formate ester which is derived from the precursor compound and which is released during use of the perfuming composition or perfumed article.

10. The method of claim 8 wherein the perfuming composition or perfumed article is an all-purpose household cleaner, a window cleaner, a furniture polish, a fabric conditioner, a softener or wash product in powder, liquid or tablet form, a shampoo, a hair conditioner, a leave-in hair conditioner, or a hairspray.

11. A perfumed article comprising a compound according to claim 1 wherein the perfumed article is provided in a perfumed product selected from the group consisting of perfume, cologne, bath gel, shower gel, hair-care product, cosmetic preparation, body deodorant, solid or liquid air freshener, detergent, fabric softener, and all-purpose cleaner.

12. The perfumed article according to claim 11 wherein the all-purpose cleaner is an all-purpose household cleaner, a window cleaner, a furniture polish, a fabric conditioner, softener or wash in form of a powder, a liquid or a tablet, a shampoo, a hair conditioner, a leave-in hair conditioner, or a hairspray.

* * * * *